US011549834B2

(12) United States Patent
Mino et al.

(10) Patent No.: US 11,549,834 B2
(45) Date of Patent: Jan. 10, 2023

(54) MULTIFUNCTIONAL ENVIRONMENTAL SENSOR DEVICE

(71) Applicant: OMRON Corporation, Kyoto (JP)

(72) Inventors: Hiroyuki Mino, Osaka (JP); Kayo Nakamura, Kusatsu (JP); Ryusuke Sakai, Kyoto (JP); Yuhei Motoki, Nagaokakyo (JP); Naotsugu Ueda, Funabashi (JP)

(73) Assignee: OMRON Corporation, Kyoto (JP)

( * ) Notice: Subject to any disclaimer, the term of this patent is extended or adjusted under 35 U.S.C. 154(b) by 309 days.

(21) Appl. No.: 16/954,346

(22) PCT Filed: Dec. 19, 2018

(86) PCT No.: PCT/JP2018/046828
§ 371 (c)(1),
(2) Date: Jun. 16, 2020

(87) PCT Pub. No.: WO2019/138822
PCT Pub. Date: Jul. 18, 2019

(65) Prior Publication Data
US 2021/0088366 A1    Mar. 25, 2021

(30) Foreign Application Priority Data
Jan. 12, 2018    (JP) .............................. JP2018-003833

(51) Int. Cl.
*G01D 21/02*     (2006.01)
*G01D 11/24*     (2006.01)
(Continued)

(52) U.S. Cl.
CPC ............ *G01D 21/02* (2013.01); *G01D 11/245* (2013.01); *G01N 33/0009* (2013.01); *H01Q 1/243* (2013.01); *H01Q 1/38* (2013.01)

(58) Field of Classification Search
CPC .. G01D 11/245; G01D 21/02; G01N 33/0009; H01Q 1/243; H01Q 1/38
See application file for complete search history.

(56) References Cited

U.S. PATENT DOCUMENTS 7,074,052 B1 *   7/2006   Ni ..................... H01R 13/6658
                                                                  361/752
2008/0150811 A1   6/2008   Honda et al.
(Continued)

FOREIGN PATENT DOCUMENTS

CN     101207229 A    6/2008
CN     103487043 A    1/2014
(Continued)

OTHER PUBLICATIONS

English tranlation JP2007212054 specification accessed from worldwide.espacenet.com Jul. 8, 2022.*
(Continued)

*Primary Examiner* — Nimeshkumar D Patel
*Assistant Examiner* — Jean F Morello
(74) *Attorney, Agent, or Firm* — Metrolex IP Law Group, PLLC

(57) ABSTRACT

A multifunctional environmental sensor device is connectable to a terminal of an electronic device for use. The sensor device includes a substrate, a plurality of different types of components mounted on the substrate and including at least a light emitter and an illuminance sensor, and a wiring pattern located on a surface of the substrate and including a contact to be in contact with the terminal of the electronic device. The light emitter is mounted on a surface of the substrate opposite to a surface of the substrate on which the illuminance sensor is mounted.

11 Claims, 11 Drawing Sheets

(51) Int. Cl.
*G01N 33/00* (2006.01)
*H01Q 1/24* (2006.01)
*H01Q 1/38* (2006.01)

(56) References Cited

U.S. PATENT DOCUMENTS

| | | |
|---|---|---|
| 2008/0154535 A1 | 6/2008 | Sparks et al. |
| 2009/0174292 A1 | 7/2009 | Takahashi et al. |
| 2009/0300379 A1 | 12/2009 | Mian et al. |
| 2012/0289080 A1 | 11/2012 | Huang et al. |
| 2013/0327143 A1 | 12/2013 | Kinoshita et al. |
| 2016/0056588 A1 | 2/2016 | Motoichi |
| 2019/0148894 A1 | 5/2019 | Motoichi |

FOREIGN PATENT DOCUMENTS

| | | |
|---|---|---|
| CN | 105390888 A | 3/2016 |
| JP | H6-300869 A | 10/1994 |
| JP | 2007-212054 A | 8/2007 |
| JP | 2009-145059 A | 7/2009 |
| JP | 2009-180587 A | 8/2009 |
| JP | 2009-180686 A | 8/2009 |
| JP | 2009-180687 A | 8/2009 |
| JP | 2010-515147 A | 5/2010 |
| JP | 2010-230691 A | 10/2010 |
| JP | 2016-31358 A | 3/2016 |
| JP | 2017-131614 A | 8/2017 |

OTHER PUBLICATIONS

English translation of the International Search Report ("ISR") of PCT/JP2018/046828 dated Jan. 29, 2019.
The Written Opinion ("WO") of PCT/JP2018/046828 dated Jan. 29, 2019.
The International Preliminary Report on Patentability (Chapter II of the Patent Cooperation Treaty) of PCT/JP2018/046828 dated Oct. 9, 2019.
The Office Action dated Jun. 24, 2021 in a counterpart Chinese patent application.

* cited by examiner

MULTIFUNCTIONAL ENVIRONMENTAL SENSOR DEVICE

FIELD

The present invention relates to a multifunctional environmental sensor device.

BACKGROUND

An environmental sensor may be used at any selected place. To use an environmental sensor at any selected place, the sensor may be connected directly to a portable electronic device having a universal serial bus (USB) terminal. Such environmental sensors are described in, for example, Patent Literatures 1 to 5, and such environmental sensors each including a USB connector connectable to a USB terminal are described in Patent Literatures 2 to 4.

CITATION LIST

Patent Literature

Patent Literature 1: Japanese Unexamined Patent Application Public n No. 6-300869
Patent Literature 2: Japanese Unexamined Patent Application Publication No. 2009-145059
Patent Literature 3: Japanese Unexamined Patent Application Publication No. 2009-180686
Patent Literature 4: Japanese Unexamined Patent Application Publication No. 2009-180687
Patent Literature 5: Japanese Unexamined Patent Application Publication No. 2010-230691

SUMMARY

Technical Problem

However, with the large USB connectors described in Patent Literatures 2 to 4, the entire environmental sensors cannot be downsized. Also, the environmental sensors have protective housings that may not be rigid and may break under an external force applied to the housings. Also, a known environmental sensor includes a single sensor or sensors of the same type, and may be replaced with a different environmental sensor to measure a different target value. The environmental sensor is thus less highly usable. The inventors have noticed that such known environmental sensors are not compact, rigid, or highly usable.

One or more aspects of the present invention are directed to an environmental sensor that is highly usable, compact, and rigid and can measure various target values.

Solution to Problem

In response to the above issue, the environmental sensor according to one or more aspects of the present invention has the structure described below.

A multifunctional environmental sensor device according to one aspect of the present invention is connectable to a terminal of an electronic device for use. The sensor device includes a substrate, a plurality of different types of components mounted on the substrate, and a wiring pattern located on a surface of the substrate and including a contact to be, in contact with the terminal of the electronic device.

The above structure allows the contact to directly connect to a universal serial bus (USB) terminal of the electronic device without a USB connector. The multifunctional environmental sensor device can thus be downsized. More specifically, the sensor device can transmit outputs from the plurality of components to the electronic device when the wiring pattern includes a circuit for transmitting the outputs from the components to the terminal of the electronic device.

In the multifunctional environmental sensor device according to the above aspect, the plurality of components may include a light emitter and an illuminance sensor, and the light emitter may be mounted on a surface of the substrate opposite to a surface of the substrate on which the illuminance sensor is mounted.

The above structure includes two oppositely functioning, components, or more specifically, the light emitter that illuminates and the illuminance sensor that detects illuminance in response to light. Light from the light emitter is blocked by the substrate, without reaching around the illuminance sensor. The substrate thus reduces the likelihood of light from the light emitter affecting illuminance detection performed by the illuminance sensor. More specifically, the sensor device is a highly usable single unit that both illuminates and detects illuminance.

The multifunctional environmental sensor device according to the above aspect may further include a cover located over and laterally above the illuminance sensor. The cover may have a surface with fine irregularities to scatter light.

The above structure causes light near the illuminance sensor to scatter on the cover surface. More specifically, external light can be easily detected by the illuminance sensor.

In the multifunctional environmental sensor device according to the above aspect, the plurality of components may further include an acceleration sensor, the substrate may be substantially rectangular, the contact may be located at a longitudinal end of the substrate, and the acceleration sensor may be mounted nearer the contact than a middle of the substrate.

The above structure can detect, when the multifunctional environmental sensor device is connected to the electronic device and used by the user, acceleration in the displacement of the electronic device. With the multifunctional environmental sensor device connected to the electronic device for use, the acceleration sensor is located near the connection between the electronic device and the multifunctional environmental sensor device. For example, the multifunctional environmental sensor device with its protruding end touched by an object is less susceptible to vibrations, thus causing less displacements of the acceleration sensor. More specifically, the acceleration sensor located as described above has an output with less noise.

The multifunctional environmental sensor device according to the above aspect may further include an antenna that communicates wirelessly with an external device. The antenna may be mounted at an end of the substrate opposite to the end at which the contact is located.

In the above structure, the antenna is less susceptible to electromagnetic waves from the electronic device or the plurality of components on the substrate, Thus, information detected by the sensors can be transmitted to an external device through the antenna. More specifically, information detected by the sensors can be transmitted to an external device through two paths, namely, the contact in the wiring pattern and the antenna, A large volume of information detected by the sensors can also be transmitted to an external device with less delays.

In the multifunctional environmental sensor device according to the above aspect, on a surface of the substrate opposite to the surface on which the contact is located, a component other than a sensor among the plurality of components may be mounted in an area opposite to an area in which the contact is located.

In the above structure, the operations of the sensors remain unaffected by heat generated by the electronic device. More specifically, the above structure allows effective use of the mounting surface of the substrate and downsizes the multifunctional environmental sensor device, without affecting the operation of the multifunctional environmental sensor device.

In the multifunctional environmental sensor device according to the above aspect, the plurality of components may further include a temperature sensor, the multifunctional environmental sensor device may further include a housing, the housing may have vents facing each other in surfaces across the substrate in a width direction, and the temperature sensor may be located between the vents.

The above structure can protect the substrate, the plurality of components, and the contact from an external impact. The structure dissipates heat outside through the vents when heat is generated by the components on the substrate or the electronic device connected to the multifunctional environmental sensor device and is dissipated toward the temperature sensor. The structure can thus reduce heat that may affect temperature detection performed by the temperature sensor.

In the multifunctional environmental sensor device according to the above aspect, the housing may include a partition separating the temperature sensor from other components.

The partition in the structure can reduce, when heat is generated by the components on the substrate or the electronic device connected to the multifunctional environmental sensor device, the likelihood of such heat being dissipated by convection toward the temperature sensor. The structure can thus reduce heat that may affect temperature detection performed by the temperature sensor.

In the multifunctional environmental sensor device according to the above aspect, the plurality of components may further include a concentration sensor that detects a concentration of a substance in an atmosphere, and a component other than the concentration sensor may be at a smallest distance from the temperature sensor.

The structure reduces the likelihood of a large amount of heat generated by the concentration sensor affecting temperature detection performed by the temperature sensor.

In the multifunctional environmental sensor device according to the above aspect, the housing may include a first housing surrounding the contact to connect to the terminal of the electronic device and a second housing accommodating the components other than the contact, the first housing may be a hollow polygonal prism, the second housing may include an engagement part engaged with an inside portion of the first housing, and the first housing and the second housing may be fixed to each other with the engagement part being engaged.

The structure includes an overlap between the first housing and the second housing near the contact. This increases the rigidity of a portion of the housing near the contact, thus enhancing the reliability of the entire multifunctional environmental sensor device.

Advantageous Effects

The environmental sensor according to the above aspects of the present invention is highly usable, compact, and rigid and can measure various target values.

DETAILED DESCRIPTION

An embodiment of the present invention (hereafter, the present embodiment) will now be described with reference to the drawings. The present embodiment described below is a mere example of the present invention in all aspects. The embodiment may be variously modified or altered without departing from the scope of the present invention. More specifically, the present invention may be implemented as appropriate using the configuration specific to each embodiment.

1. Example Use

Figure 1A:
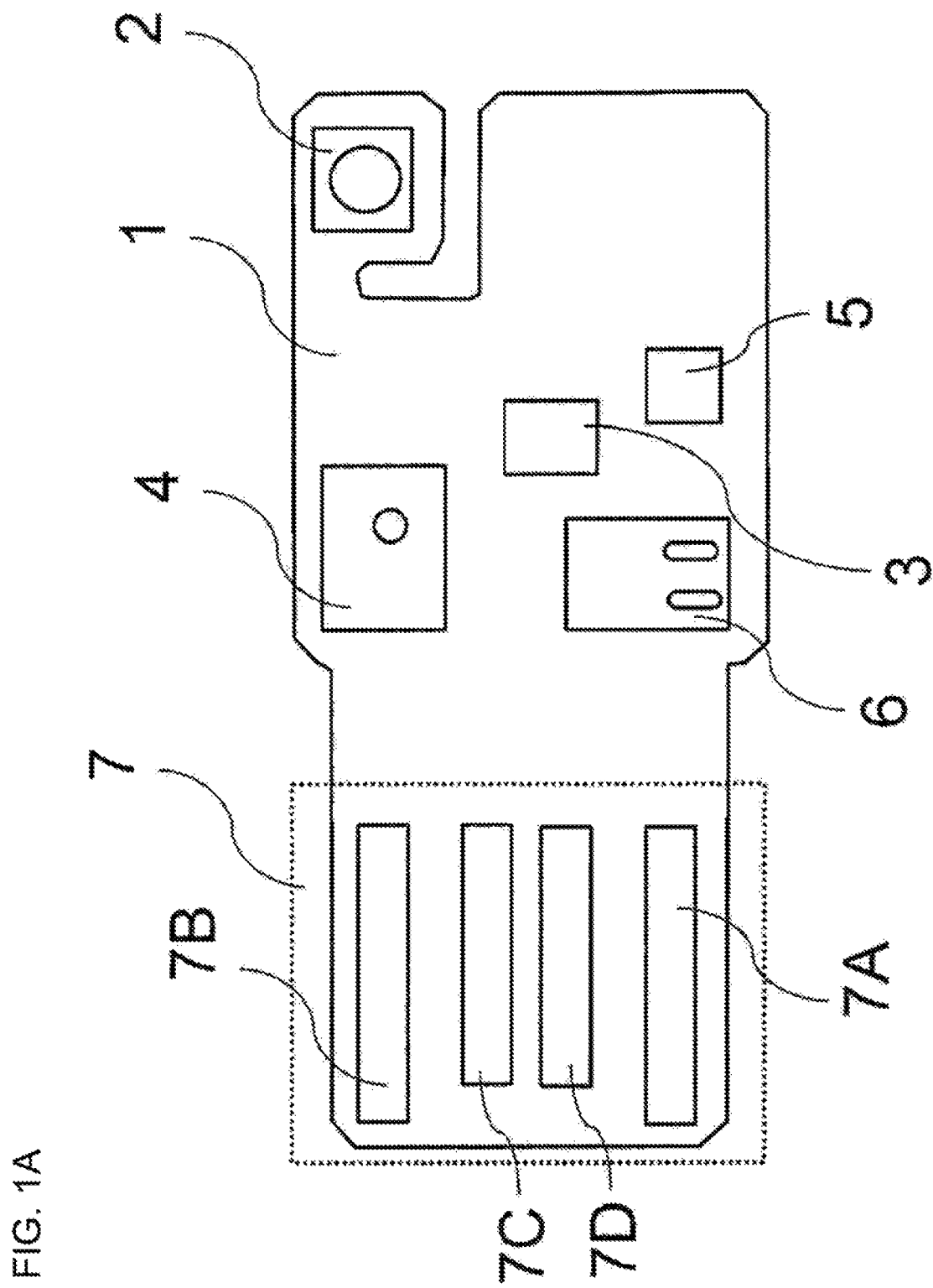
FIG. 1A is a schematic diagram of an, example substrate included in a multifunctional environmental sensor device according to an embodiment showing a front surface on which components are mounted.
Figure 1B:
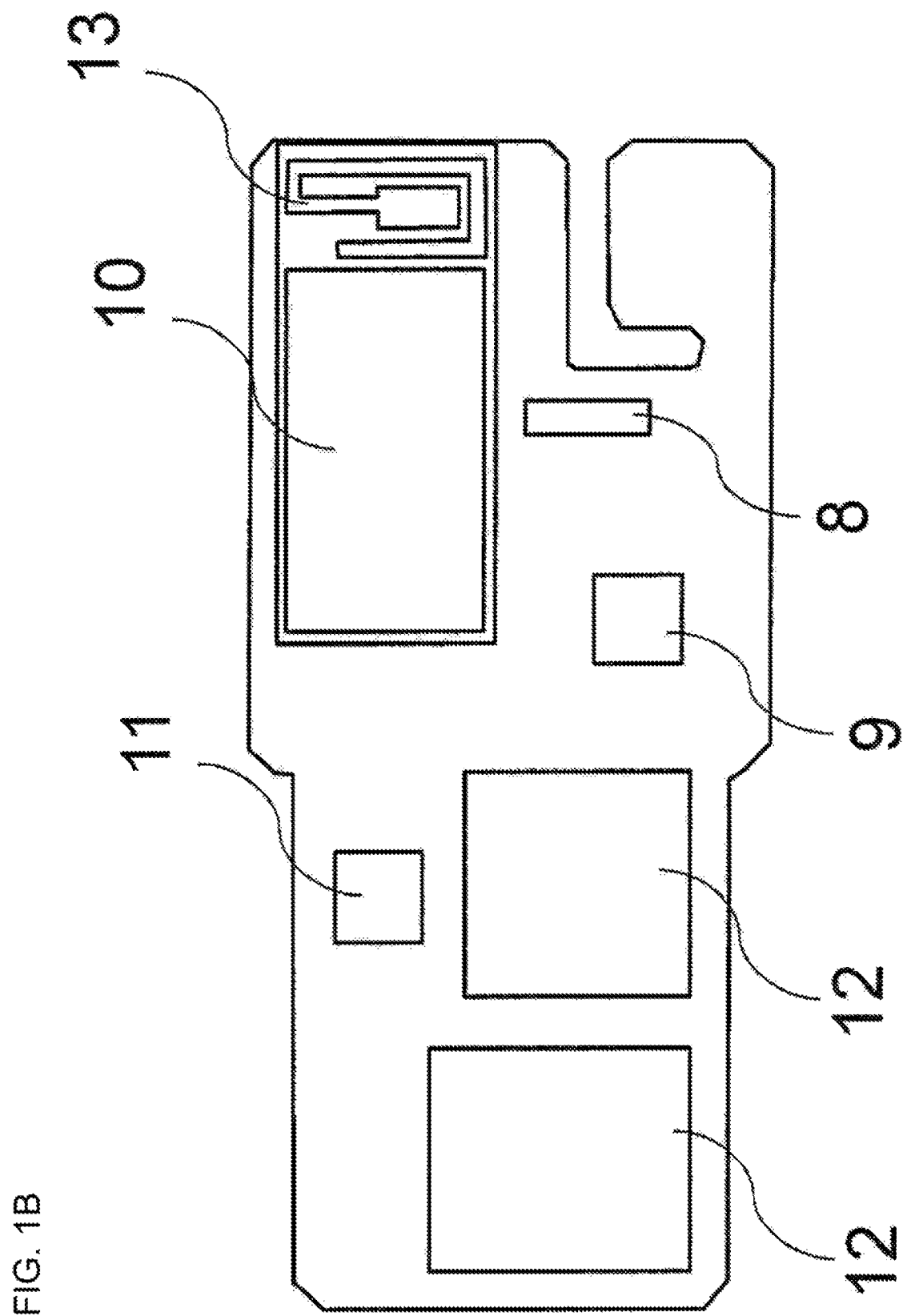
FIG. 1B is a schematic diagram of the example substrate included in the multifunctional environmental sensor device according to the embodiment showing a back surface on which components are mounted.

One example use of a multifunctional environmental sensor device according to one embodiment of the present invention will now be described with reference to FIGS. 1A and 18. FIGS. 1A and 1B are schematic diagrams of sensors included in a multifunctional environmental sensor device 100 according to the present embodiment. The multifunctional environmental sensor device 100 includes a substrate 1. FIG. 1A is a schematic diagram of the substrate 1 showing a front surface. FIG. 1B is a schematic diagram of the substrate 1 showing a back surface. As shown in FIG. 1A, the multifunctional environmental sensor device 100 includes, on the front surface of the substrate 1, a temperature and humidity sensor 2 for detecting temperature and humidity and an absolute pressure sensor 3 for detecting atmospheric pressure. The multifunctional environmental sensor device 100 also includes a microphone 4 for detecting sound, an illuminance sensor 5 for detecting illuminance, and, a volatile organic compound (VOC) sensor 6 for detecting the concentrations of VOCs in the atmosphere.

Although not shown, the substrate 1 includes a wiring pattern for transmission of signals complying with the universal serial bus (USB) standard. The substrate 1 includes, on the front surface, a contact 7 connected to the wiring pattern. The contact 7 is a flat metal plate.

As shown in FIG. 1B, the multifunctional environmental sensor device 100 includes, on the back surface of the substrate 1, a light emitting diode (LED) 8 that illuminates upon detecting the operations of components in the multifunctional environmental sensor device 100 and an acceleration sensor 9 that detects acceleration in the displacement of the sensor. The multifunctional environmental sensor device 100 also includes a Bluetooth Low Energy (BLE) module 10 that communicates with an external device based on Bluetooth (registered trademark) communication. The multifunctional environmental sensor device 100 also includes a voltage regulator 11 and components 12. The BLE module 10 includes an antenna 13 that transmits and receives radio waves. Although the LED 8 is connected to the BLE module 10 to illuminate in this example, the LED 8 may detect an operation of a specific sensor to illuminate.

As described above, the multifunctional environmental sensor device 100 according to the present embodiment can detect various physical quantities, such as temperature and humidity, pressure, sound, illuminance, the concentrations of VOCs in the atmosphere, the operations of components, and the displacement of a sensor. The multifunctional environmental sensor device 100 is thus highly usable. The multifunctional environmental sensor device 100 is connectable to an electronic device including a USB terminal through the flat plate contact 7 located on the front surface of the substrate 1. The multifunctional environmental sensor device 100 thus includes no USB connector and is compact.

2. Example Structure

Hardware Configuration

An example multifunctional environmental sensor device according to the present embodiment will now be described. A multifunctional environmental sensor device 100 according to the present embodiment is connectable to, for example, an electronic device including a USB terminal when in use. As shown in FIG. 1A, the multifunctional environmental sensor device 100 includes, on the front surface of a substantially rectangular substrate 1, a temperature and humidity sensor 2 for detecting temperature and humidity and an absolute pressure sensor 3 for detecting atmospheric pressure. The substrate 1 has a thickness of, for example, 0.8 mm. The temperature and humidity sensor 2 is an example of a temperature sensor in an aspect of the present invention. The absolute pressure sensor 3 is an example of a pressure sensor in an aspect of the present invention. The temperature and humidity sensor 2 is mounted at an end of the front surface of the substrate 1 in a longitudinal direction. The substrate 1 has an L-shaped cutout near and surrounding the temperature and humidity sensor 2.

The multifunctional environmental sensor device 100 also includes a microphone 4 for detecting sound, an illuminance sensor 5 for detecting illuminance, and a VOC sensor 6 for detecting the concentrations of VOCs in the atmosphere. The VOC sensor 6 is an example of a concentration sensor in an aspect of the present invention. The VOC sensor 6 is mounted on the front surface of the substrate 1 to be farthest possible from the temperature and humidity sensor 2. For example, the absolute pressure sensor 3, the microphone 4, and the illuminance sensor 5 are mounted between the temperature and humidity sensor 2 and the VOC sensor 6. The above components mounted on the front surface of the substrate 1 may each have a height from the front surface to the upper surface, to be or to fall below, for example, 1.1 mm.

Although not shown, the substrate 1 includes a wiring pattern for transmission of signals complying with the USB standard. More specifically, the wiring pattern includes signal lines VBUS and ground (GND) for a power source. The wiring pattern also includes signal lines D+ and D− for data communication. The substrate 1 includes, on the front surface, a contact 7 connected to the wiring, pattern for transmission of signals complying with the USB standard. More specifically, the contact 7 includes a contact 7A connectable to VBUS, a contact 7B to GND, a contact 7C to D+, and a contact 70 to D−. The contact 7 is located at the other end of the substrate 1 in the longitudinal direction, opposite to the end at which the temperature and humidity sensor 2 is mounted. The contact 7 is a flat metal plate. The contact 7 is uncovered on the front surface of the substrate 1.

As shown in FIG. 1B, the multifunctional environmental sensor device 100 includes an LED 8 on the back surface of the substrate 1. The LED 8 is an example of a light emitter in an aspect of the present invention.

As shown in FIG. 1B, the multifunctional environmental sensor device 100 also includes, on the back surface of the substrate 1, an acceleration sensor 9 for detecting acceleration in the displacement of the sensor. The acceleration sensor 9 is mounted near the contact 7 located on the front surface of the substrate 1.

The multifunctional environmental sensor device 100 also includes a BLE module 18 for communication with an external device based on Bluetooth communication. The LED 8 is connected to the BLE module 10 to illuminate. The BLE module 10 includes an antenna 13 that transmits and receives radio waves. The antenna 13 is mounted, on the back surface of the substrate 1, at the end opposite to the end with the contact 7. Bluetooth communication is an example of wireless communication in an aspect of the present invention. The multifunctional environmental sensor device 100 also includes a voltage regulator 11 and components 12. The voltage regulator 11 and the components 12 are each an example of a component other than a sensor among the plurality of components in an aspect of the present invention. The voltage regulator 11 may convert, for example, a voltage from 5 V to 3.3 V. The components 12 are components other than sensors. The voltage regulator 11 and the components 12 are less susceptible to ambient heat. The voltage regulator 11 and the components 12 are mounted on the back surface of the substrate 1 directly, opposite to the contact 7. The components including the various sensors mounted on the back surface of the substrate 1 each have a height from the back surface to the upper surface to b or to fall below, for example, 1.3 mm.

Figure 2:
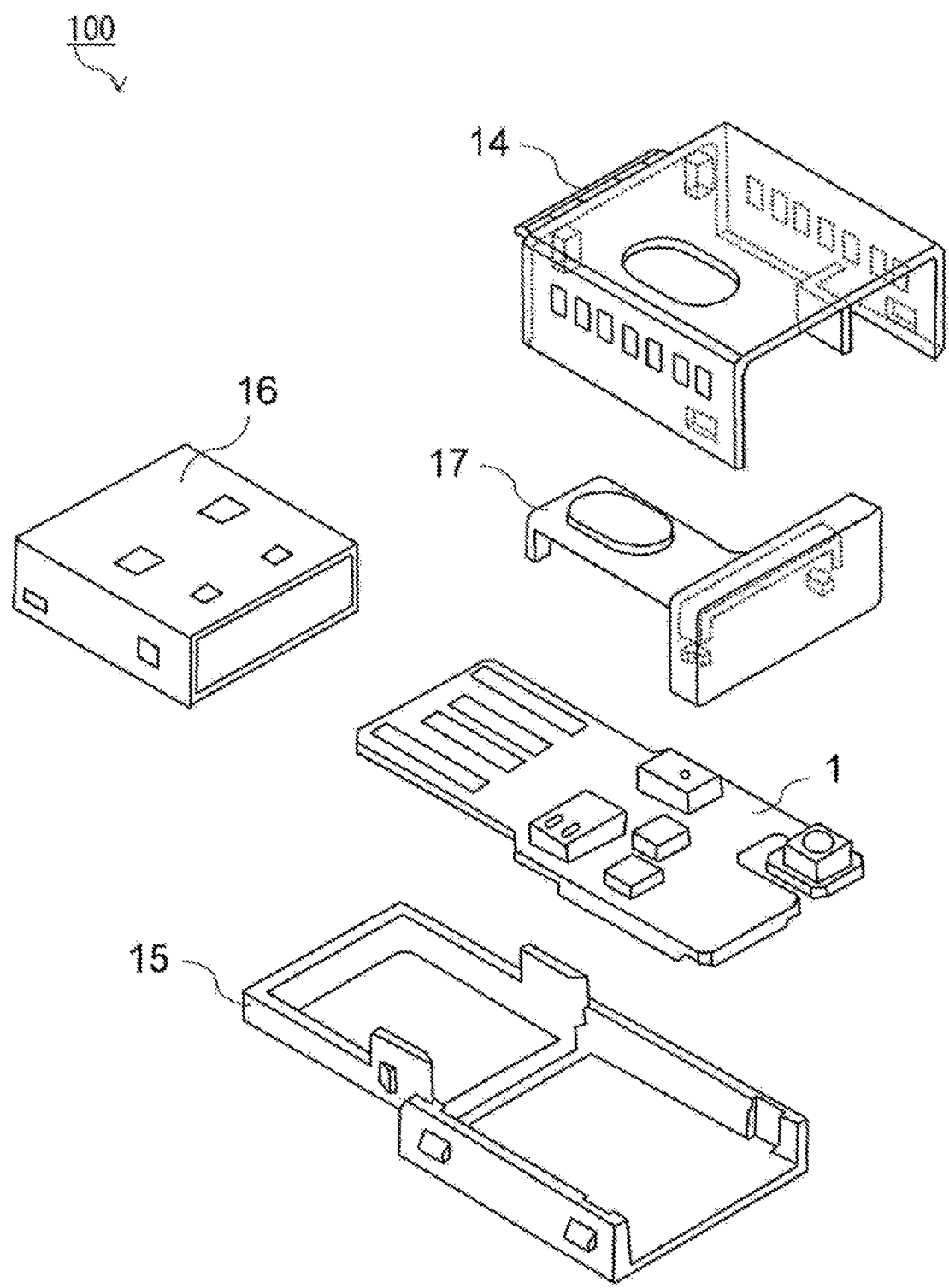
FIG. 2 is an example schematic exploded perspective view of the multifunctional environmental sensor device.

The multifunctional environmental sensor device 100 includes a case, accommodating the substrate 1 and the components on the substrate 1. FIG. 2 is an example schematic exploded perspective view of the multifunctional environmental sensor device 100. The multifunctional environmental sensor device 100 includes a front case 14 covering the components including the sensors mounted on the front surface of the substrate 1 and a rear case 15 covering the components including the sensors mounted on the back surface of the substrate 1. The multifunctional environmental sensor device 100 also includes a USB cover 16 covering the two surfaces of a portion of the substrate 1 near the contact 7. The multifunctional environmental sensor device 100 also includes a light cover 17 located on a side surface of the substrate 1 and over the illuminance sensor 5. A housing in an aspect of the present invention includes the front case 14, the rear case 15, and the USB cover 16. The USB cover 16 is an example of a first housing in an aspect of the present invention. The front case 14 is an example of a second housing in an aspect of the present invention.

Figure 3:
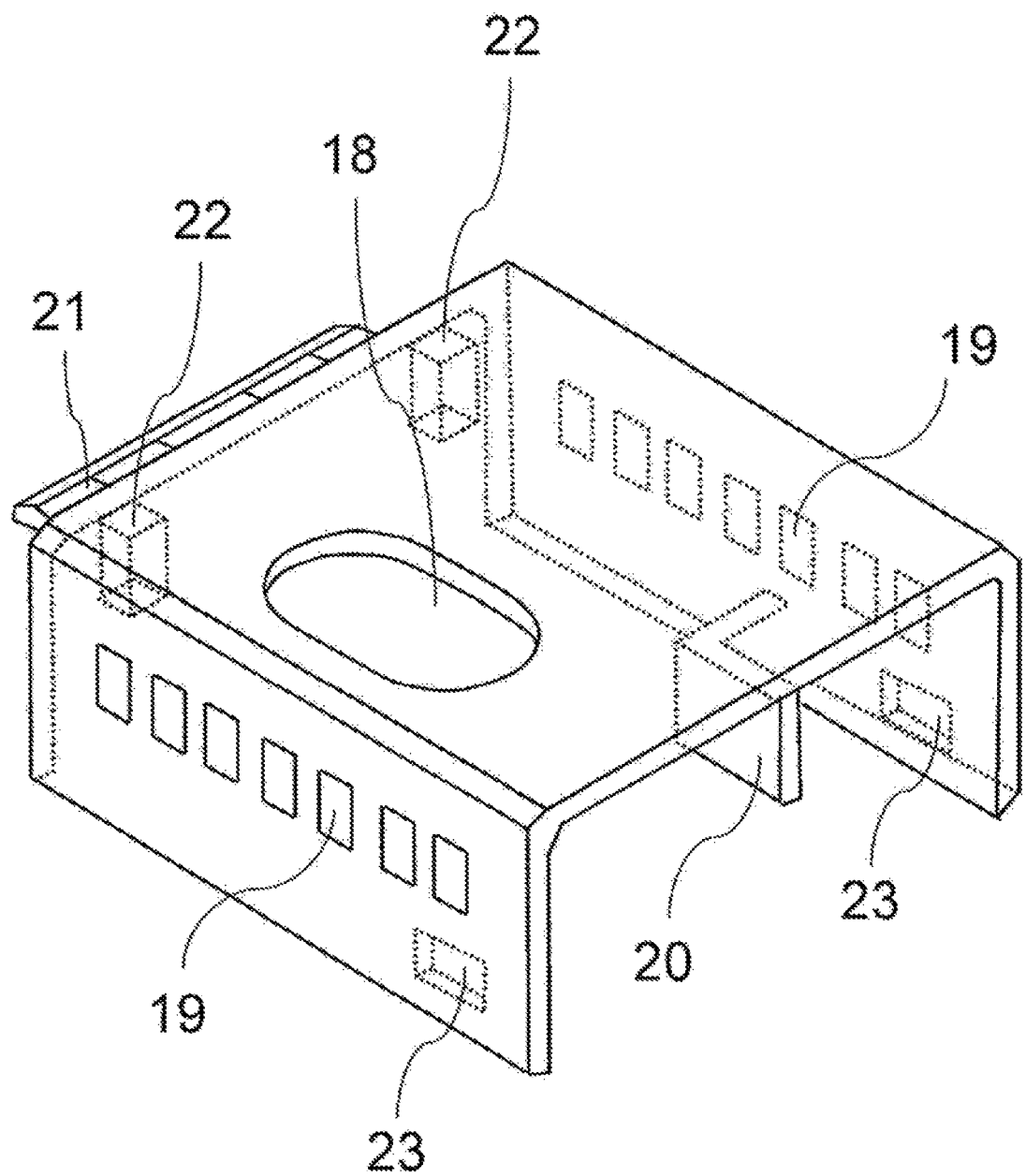
FIG. 3 is a schematic diagram of an example front case.

FIG. 3 is a schematic diagram of an example of the front case 14. The front case 14 is a molded product formed from a resin, such as acrylonitrile butadiene styrene (ABS). The front case 14 has an opening 18 in its upper surface. The opening 18 is, for example, oval. The front case 14 has vents 19 in two facing side surfaces. The front case 14 includes an L-shaped partition 20 extending downward from the upper surface. The front case 14 also includes an extension 21 extending parallel to the upper surface from near the upper surface. The extension 21 is an example of an engagement part in an aspect of the present invention. The front case 14 also includes extensions 22 near the extension 21. The extensions 22 extend perpendicularly to the upper surface from near the upper surface. The front case 14 has recesses 23 on the inner surfaces. The upper surface of the front case 14 has a length of, for example, about 15.1 mm and a width of, for example, about 14.9 mm. The front case 14 has a height of, for example, about 7 mm.

Figure 4:
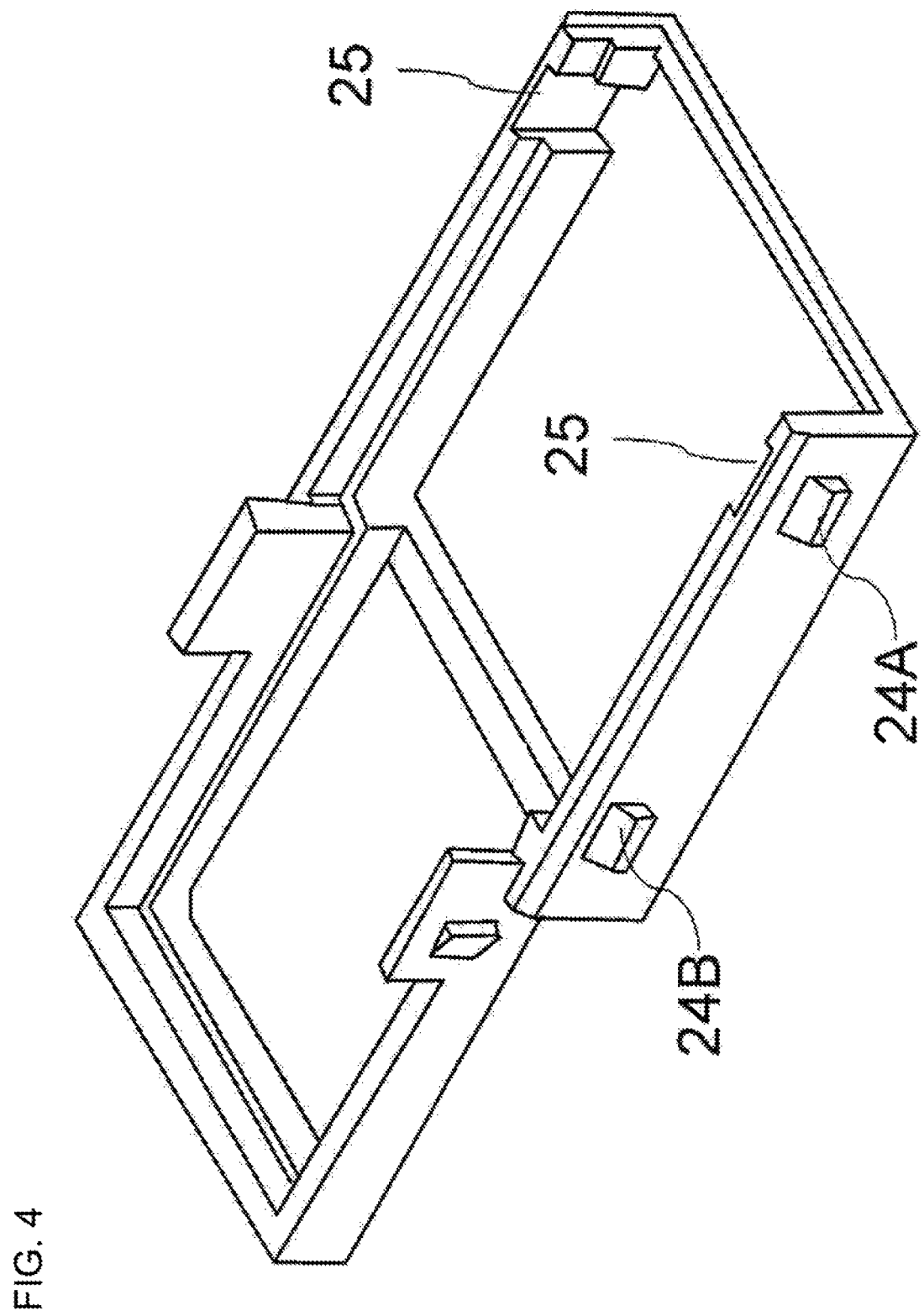
FIG. 4 is a schematic diagram of an example rear case.

FIG. 4 is a schematic diagram of an example of the rear case 15. Similarly to the front case 14, the rear case 15 is a molded product formed from a resin, such as ABS. The rear case 15 includes tabs 24A and 24B on the outer surfaces of two side surfaces. The rear case 15 has recesses 25 on the inner surfaces of the two side surfaces.

Figure 5:
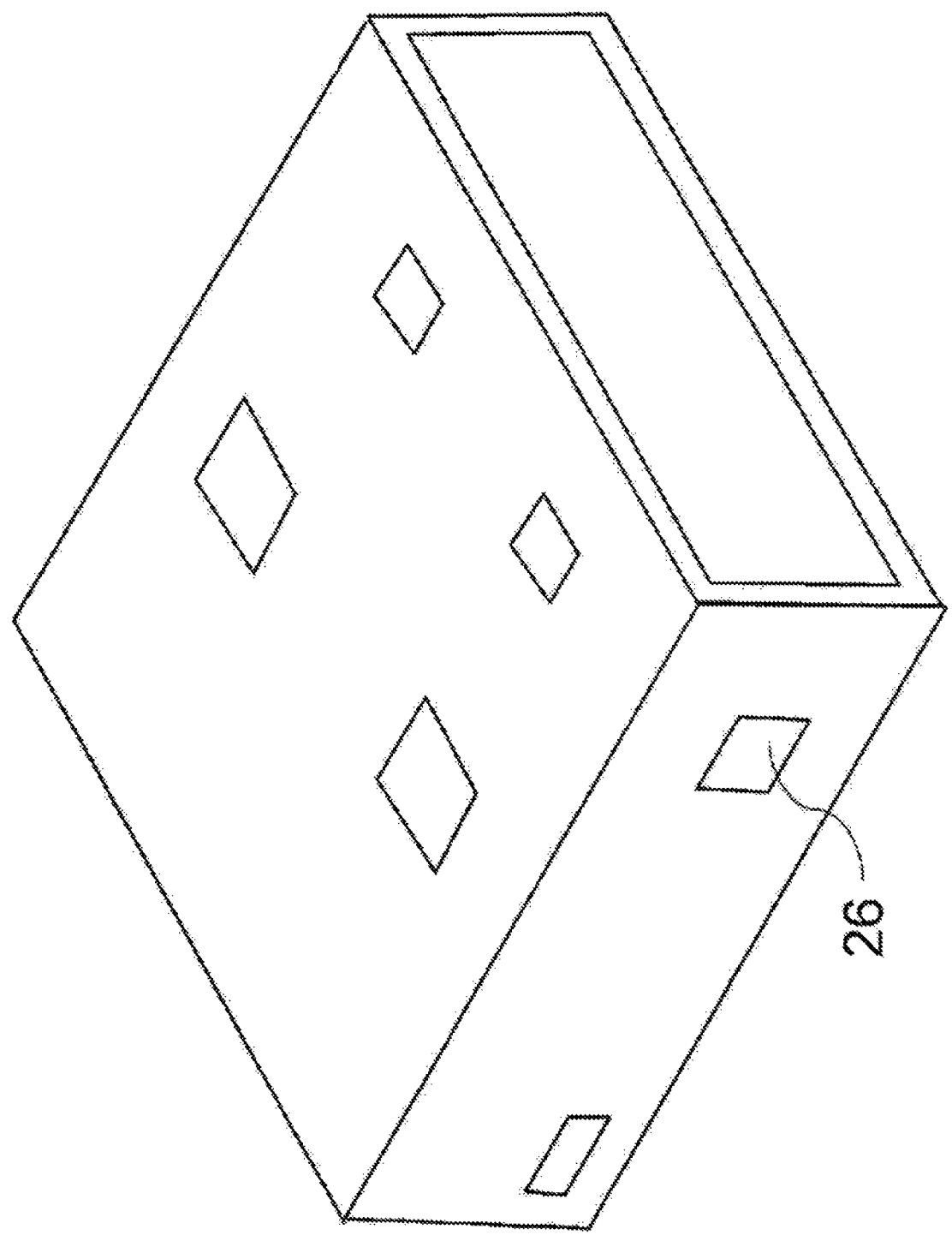
FIG. 5 is a schematic diagram of an example universal serial bus (USB) cover.

FIG. 5 is a schematic diagram of an example of the USB cover 16. The USB cover 16 is substantially a hollow polygonal prism and has a rectangular cross section as viewed in an axial direction. The USB cover 16 includes a cold rolled steel sheet (steel plate cold commercial or SPCC). The surface of the USB cover 16 is plated with nickel. The USB cover 16 has openings 26 in two side surfaces. The USB cover 16 has a square upper surface with a side of about 12 mm. The USB cover 16 has a height of about 4.5 mm.

Figure 6:
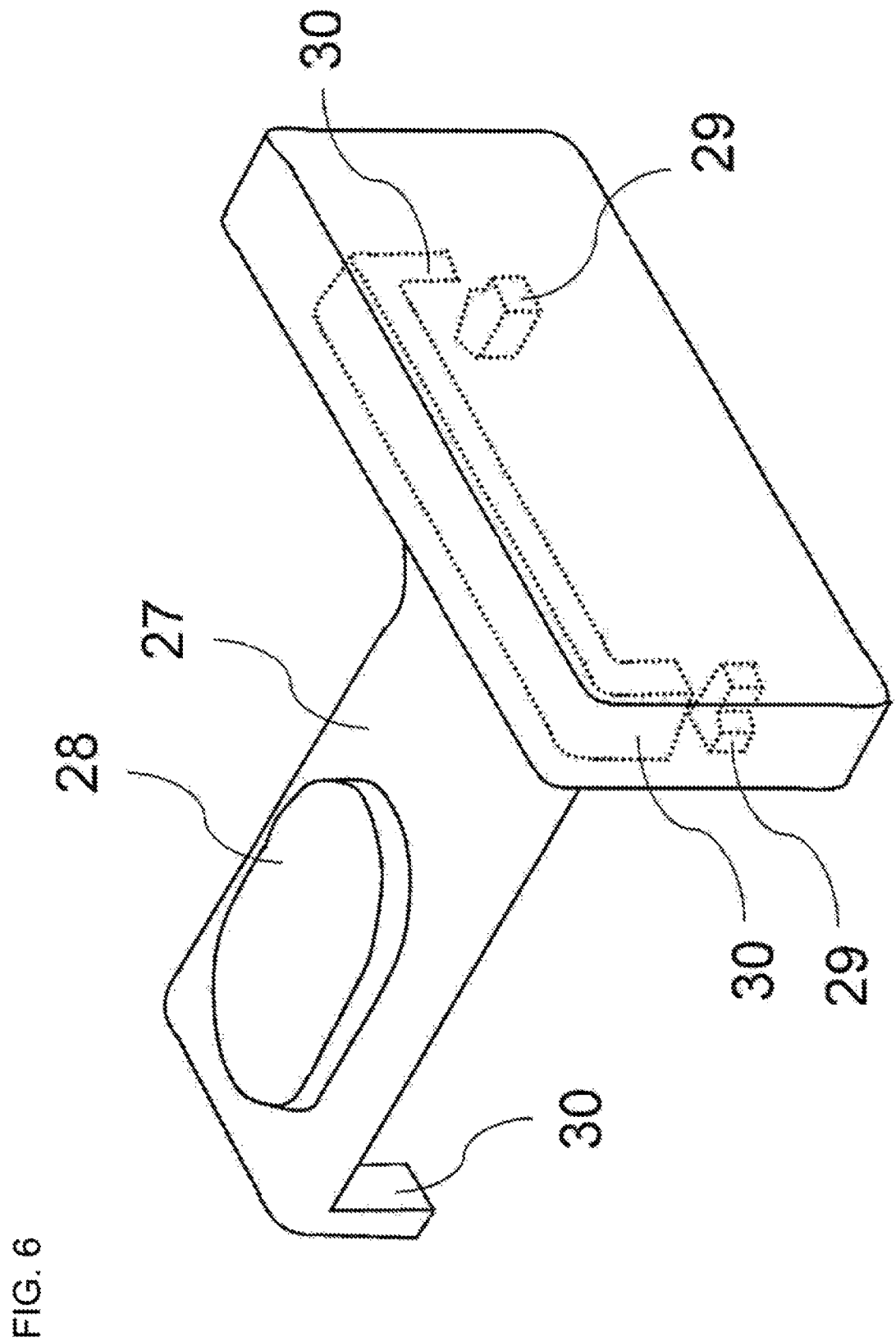
FIG. 6 is a schematic diagram of an example light cover.

FIG. 6 is a schematic diagram of an example of the light cover 17. The light cover 17 is a molded product formed from a resin, such as polycarbonate. The light cover 17 transmits at least a predetermined amount of light to provide intended sensor sensitivity. For example, the light cover 17 has fine irregularities on the surface and is milk white. The light cover 17 has an upper surface 27 and an oval protrusion 28 on a portion of the upper surface 27. The protrusion 28 is located above the illuminance sensor 5 mounted on the substrate 1 when the light cover 17 is attached to the substrate 1. The light cover 17 integrally includes a section to be located above the illuminance sensor 5 and a section to be located near the LED 8 to transmit light from the LED 8. The light cover 17 includes two tabs 29 extending laterally from its side surface. The light cover 17 also includes three extensions 30 extending downward from the upper surface 27.

Figure 7:
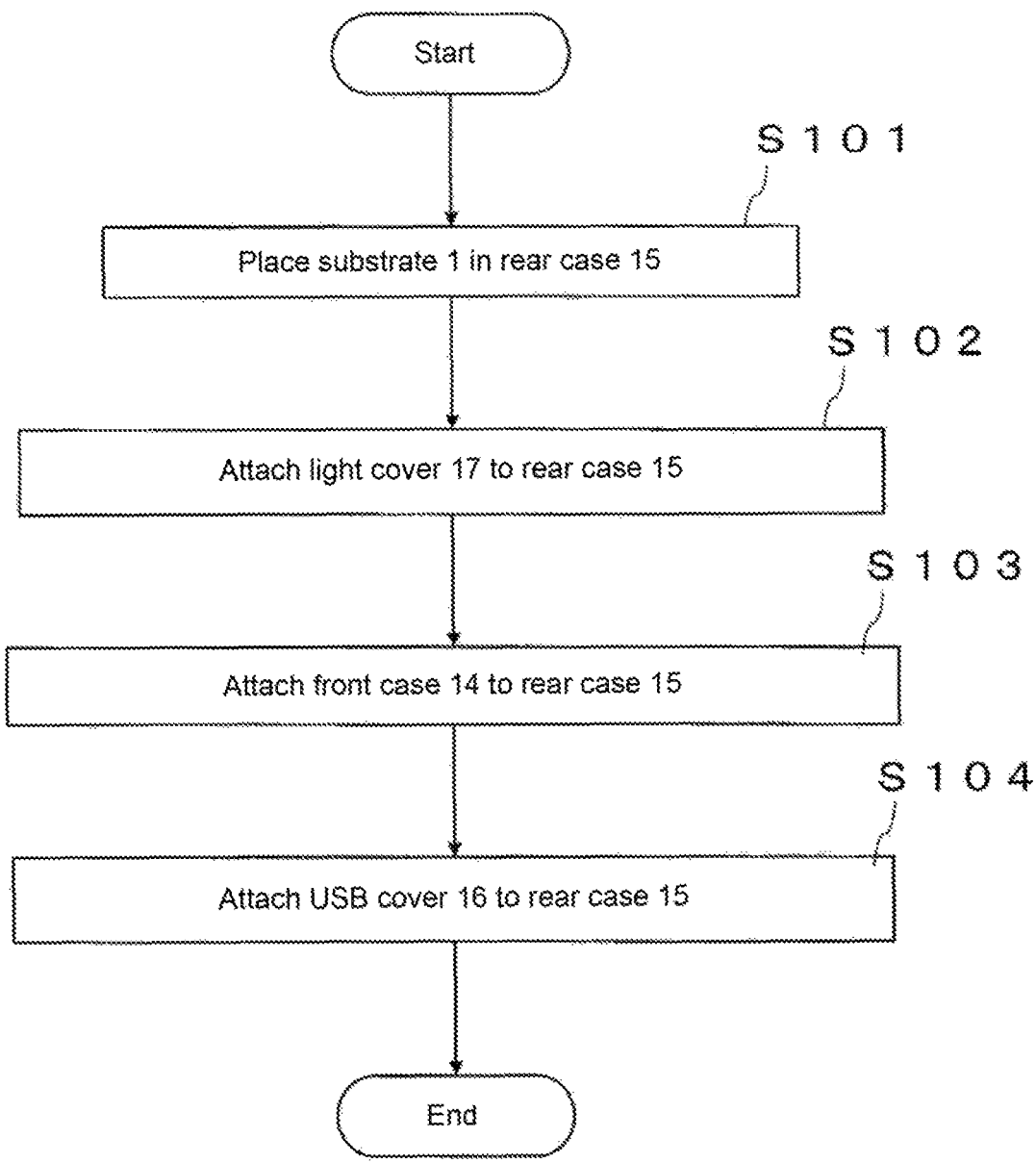
FIG. 7 is a flowchart showing an example assembling procedure.

An example procedure for assembling the front case 14, the rear case 15, the USB cover 16, and the light cover 17 will now be described. FIG. 7 is a flowchart showing an example assembling procedure. The assembling procedure described below is a mere example, and each step may be modified. In the assembling procedure described below, steps may be eliminated, substituted, or added as appropriate depending on each embodiment.

Step S101

In step S101, the substrate 1 is placed in the rear case 15. When the substrate 1 is placed in the rear case 15, the upper surfaces of the components mounted on the back surface of the substrate 1 are in contact with the lower surface of the rear case 15.

Step S102

In step S102, the light cover 17 is attached to the rear case 15. The light cover 17 is attached to the right side surface of the substrate 1 to have the protrusion 28 located above the illuminance sensor 5 mounted on the substrate 1. The light cover 17 is fixed to the rear case 15 with the tabs 29 engaged with the recesses 25 on the inner surfaces of the rear case 15. When the light cover 17 is fixed to the rear case 15, the extensions 30 on the light cover 17 are in contact with the front surface of the substrate 1, placing the substrate 1 in position.

Step S103

In step S103, the front case 14 is attached to the rear case 15. The opening 18 in the front case 14 is first fitted around the protrusion 28 on the light cover 17. The recesses 23 on the front case 14 are engaged with the tabs 24A on the rear case 15. This fixes the front case 14 to the rear case 15. When the front case 14 is fixed to the rear case 15, the extensions 22 on the front case 14 are in contact with the front surface of the substrate 1. The L-shaped partition 20 included in the front case 14 is placed through the L-shaped cutout in the substrate 1 to be located between the temperature and humidity sensor 2 and the components other than the temperature and humidity sensor 2. The vents 19 are located near the temperature and humidity sensor 2, the microphone 4, and the VOC sensor 6.

Step S104

In step S104, the USB cover 16 is attached to the fear case 15. The USB cover 16 is fixed to the rear case 15 with the openings 26 engaged with the tabs 24B on the rear case 15. The USB cover 16 fixed to the rear case 15 covers the contact 7 mounted on the front surface of the substrate 1 and the voltage regulator 11 and the components 12 mounted on the back surface of the substrate 1. The extension 21 on the front case 14 is placed under the upper surface of the USB cover 16. The extension 21 and the USB cover 16 thus overlap and fixed to each other. After assembled completely, the multifunctional environmental sensor device 100 has a maximum thickness of, for example, about 7 mm.

3. Operation Example

Figure 8:
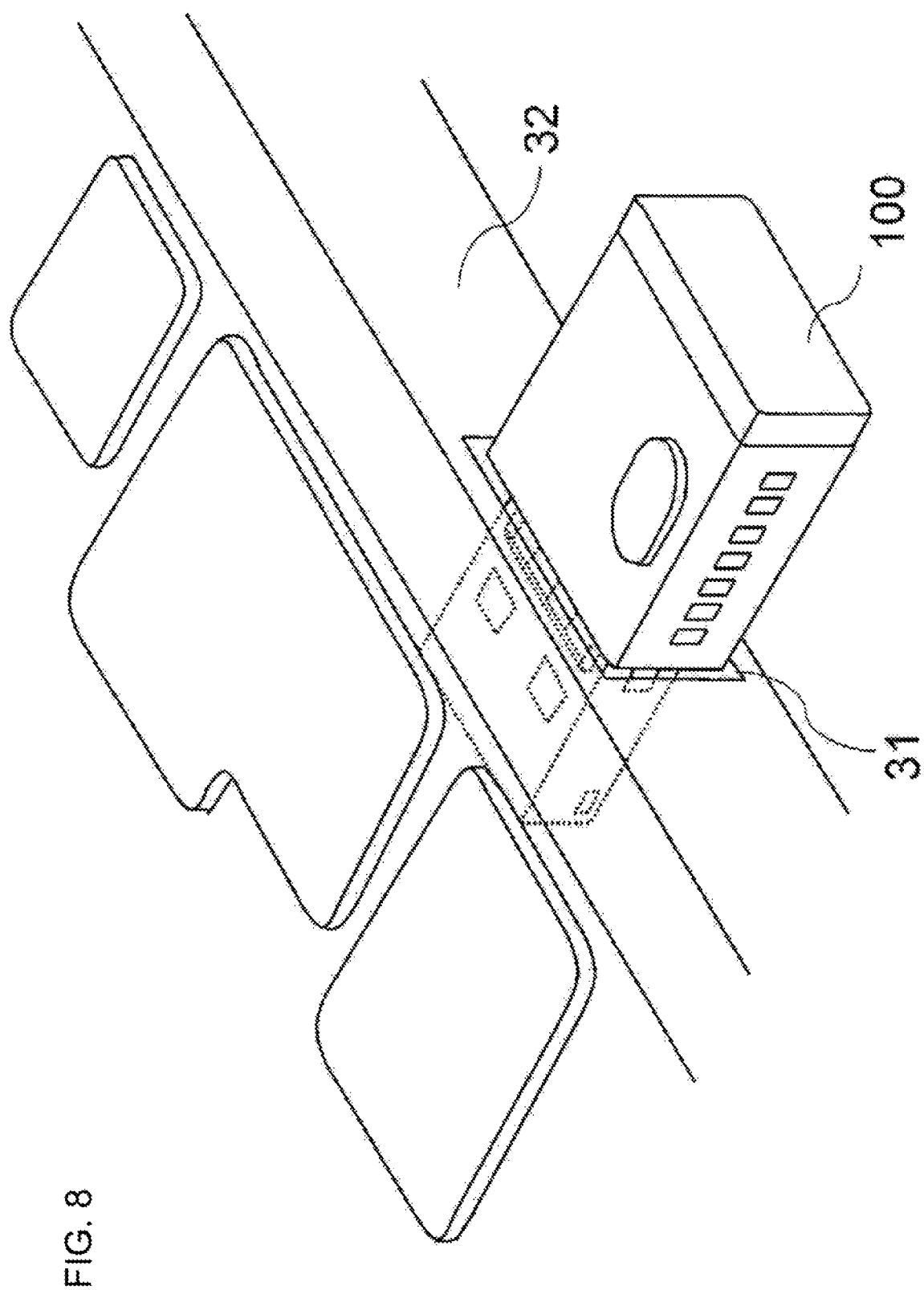
FIG. 8 is a schematic diagram of the multifunctional environmental sensor device in an example use.

An operation example of the multifunctional environmental sensor device 100 will now be described with reference to FIG. 8. FIG. 8 is a diagram of the multifunctional environmental sensor device 100 connected to a laptop computer 32 including a USB terminal port 31 including a USB terminal in an example use. When connected to the laptop computer 32, the multifunctional environmental sensor device 100 receives, from the USB terminal in the laptop computer 32, electric power supplied to the wiring pattern on the substrate 1 through the contact 7A. The voltage regulator 11 reduces the voltage, for example, from 5 V to 3.3 V. The electric power with the voltage of 3.3 V is then supplied to the components including the sensors mounted on the substrate 1.

Each component starts operating when energized. For example, the temperature and humidity sensor 2 mounted on the front surface of the substrate 1 detects ambient temperature and humidity. The multifunctional environmental sensor device 100 transmits the detected temperature and humidity information to the laptop computer 32 through the contact 7. The temperature and humidity information transmitted to the laptop computer 32 may be stored into a storage (not shown) in the laptop computer 32. The temperature and humidity information may appear on the display of the laptop computer 32.

The absolute pressure sensor 3 mounted on the front surface of the substrate 1 detects atmospheric pressure. The multifunctional environmental sensor device 100 transmits the detected pressure information to the laptop computer 32 through the contact 7. The pressure information transmitted to the laptop computer 32 may be stored into the storage (not shown) in the laptop computer 32. The pressure information may appear on the display of the laptop computer 32.

The microphone 4 mounted on the front surface of the substrate 1 detects ambient sound. The multifunctional environmental sensor device 100 transmits the detected sound information to the laptop computer 32 through the contact 7. The sound information transmitted to the laptop computer 32 may be stored into the storage (not shown) in the laptop computer 32. The sound information may appear on the display of the laptop computer 32.

The VOC sensor 6 mounted on the front surface of the substrate 1 detects the concentration of a substance in the atmosphere. The multifunctional environmental sensor device 100 transmits the detected concentration information to the laptop computer 32 through the contact 7. The concentration information transmitted to the laptop computer 32 may be stored into the storage (not shown) in the laptop computer 32. The concentration information may appear on the display of the laptop computer 32.

Ambient light around the multifunctional environmental sensor device 100 is incident on the light cover 17. Light incident on the light cover 17 scatters on the surface of the light cover 17 and is detected by the illuminance sensor 5. The illuminance information detected by the illuminance sensor 5 is transmitted to the laptop computer 32 through the contact 7. For example, the laptop computer 32 automatically controls, based on the illuminance information detected by the illuminance sensor 5, the brightness of the display of the laptop computer 32. For the laptop computer 32 including a keyboard with illuminating characters, the laptop computer 32 may also automatically control the amount of illumination of the characters based on the information detected by the illuminance sensor 5. The illuminance information transmitted to the laptop computer 32 may be stored into the storage (not shown) in the laptop computer 32. The illuminance information may appear on the display of the laptop computer 32.

The acceleration sensor 9 mounted on the back surface of the substrate 1 detects acceleration in the displacement of the sensor. The multifunctional environmental sensor device 100 transmits the detected acceleration information to the laptop computer 32 through the contact 7. The acceleration information transmitted to the laptop computer 32 may be stored into the storage (not shown) in the laptop computer 32. The acceleration information may appear on the display of the laptop computer 32.

The acceleration sensor 9 detects more information than the other sensors. For the laptop computer 32 including a module enabling Bluetooth communication, the multifunctional environmental sensor device 100 may wirelessly transmit the information detected by each sensor other than the acceleration sensor 9 to the laptop computer 32 through the antenna 13 in the BLE module 10, rather than through the contact 7.

The LED 8 mounted on the back surface of the substrate 1 is connected to the BLE module 10 to obtain information about the operation of the BLE module 10. The LED 8 illuminates when the BLE module 10 is operating. The LED 8 is located rightward from the middle on the back surface of the substrate 1. Light from the LED 8 passes through near the back surface of the substrate 1 and is incident on a portion of the light cover 17 on the right side surface of the substrate 1. The light diffuses within the light cover 17 and is then released outside.

ADVANTAGES AND EFFECTS

As described above, the multifunctional environmental sensor device 100 according to the present embodiment can detect various physical quantities, such as temperature and humidity, pressure, sound, illuminance, the concentrations of VOCs in the atmosphere, the operations of components, and the displacement of a sensor. The multifunctional environmental sensor device 100 is thus highly usable.

The multifunctional environmental sensor device 100 includes the flat plate, contact 7 on the front surface of the substrate 1 to directly receive electric power supplied from the laptop computer 32 for operating the components including the sensors mounted on the substrate 1. Information detected by each sensor, is transmitted to the laptop computer 32 through the contact 7. The detected information may appear on the laptop computer 32. More specifically, the multifunctional environmental sensor device 100 includes no USB connector and thus is compact.

The multifunctional environmental sensor device 100 includes two oppositely functioning components, or more specifically, the LED 8 that illuminates upon detecting the operations of components in the multifunctional environmental sensor device 100 and the illuminance sensor 5 that detects illuminance in response to light. The LED 8 and the illuminance sensor 5 are mounted on the opposing front and back surfaces of the substrate 1. Light from the LED 8 is blocked by the substrate 1, without reaching around the illuminance sensor 5. More specifically, the multifunctional environmental sensor device 100 can reduce such light affecting illuminance detection performed by the illuminance sensor 5. Also, the multifunctional environmental sensor device 100 is a highly usable single unit that both illuminates and detects illuminance.

The light cover 17 can diffuse light from the LED 6, The user can thus easily perceive light from the LED 8 and easily determine the operating state of each component.

External light incident on the light cover 17 scatters on the surface of the light cover 17 before being detected by the illuminance sensor 5, The laptop computer 32 automatically controls the illuminance of the display based on the illuminance information detected by the illuminance sensor 5. The laptop computer 32 can save energy.

The multifunctional environmental sensor device 100 includes the acceleration sensor 9 that detects acceleration in the displacement of the sensor. For example, when the user accidentally drops the laptop computer 32, the multifunctional environmental sensor device 100 can stop reading from and writing to the hard disk drive in the laptop computer 32 and can retract the magnetic head in the hard disk drive. This reduces breakdown of the hard disk drive.

Figure 9:
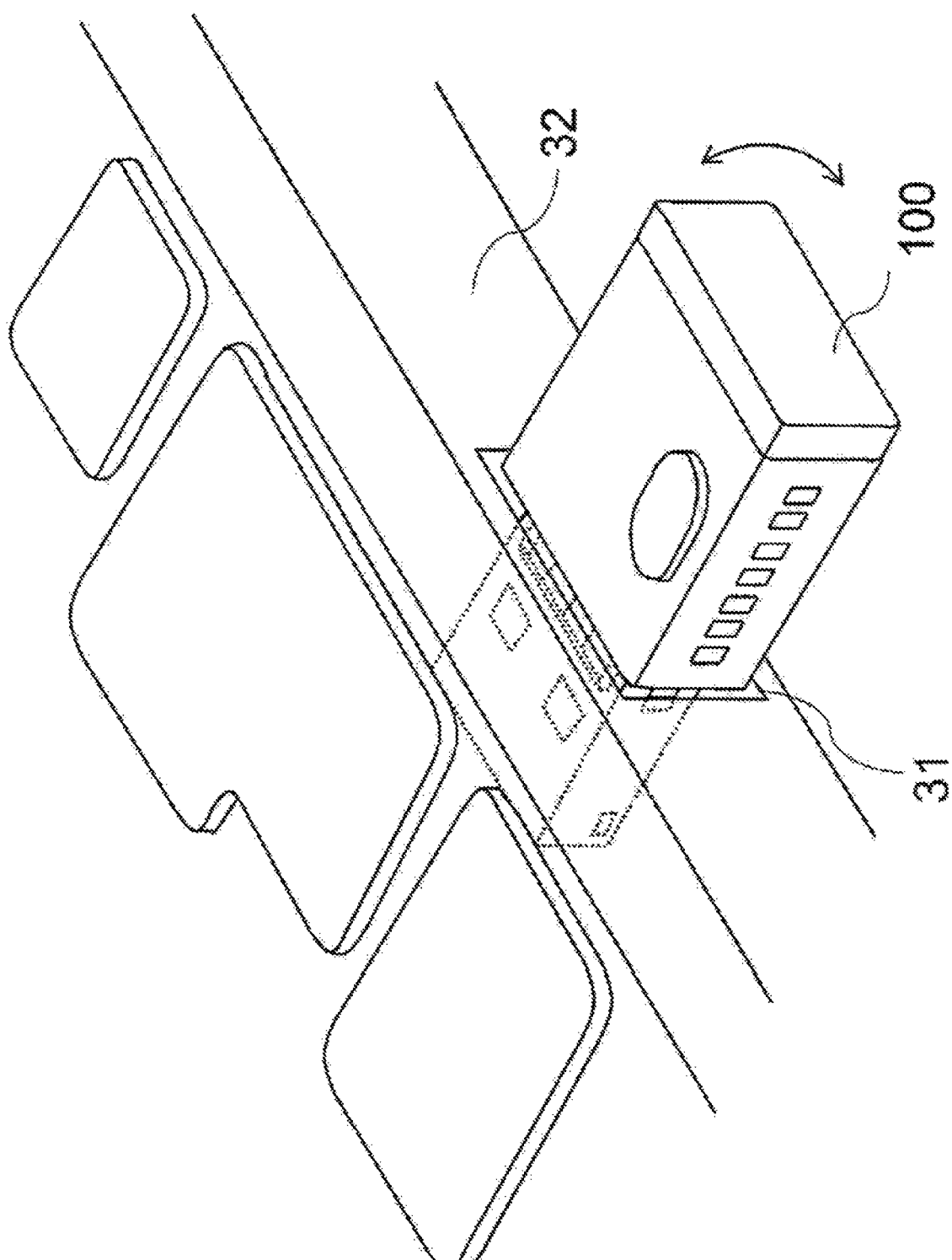
FIG. 9 is a schematic diagram of the multifunctional environmental sensor device with its protruding end accidentally touched by a hand or another part.

FIG. 9 is a schematic diagram of the multifunctional environmental sensor device 100 inserted in the USB terminal port 31 in an example use, with its protruding end accidentally touched by a hand or another part. When accidentally touched by a hand or another part, the protruding end of the multifunctional environmental sensor device 100 is moved forcibly. However, the multifunctional environmental sensor device 100 inserted in the USB terminal port 31 retains a portion of the substrate 1 near the USB terminal port 31 to be substantially immovable. More specifically, the acceleration sensor 9 mounted near the contact 7 has less displacements. This reduces noise in the output from the acceleration sensor 9.

The voltage regulator 11 and the components 12 are mounted near the contact 7 at a small distance to the laptop computer 32. Thus, the operations of the sensors mounted on the substrate 1 remain unaffected by heat generated by the laptop computer 32. More specifically, the voltage regulator 11 and the components 12 are located to allow effective use of the mounting surface of the substrate 1 and downsize the multifunctional environmental sensor device 100.

The antenna 13 included in the BLE module 10 is located, on the back surface, at the distal end of the substrate 1 opposite to the end with the contact 7. The antenna 13 is less susceptible to electromagnetic waves from the components including the sensors mounted on the substrate 1 and the laptop computer 32, reducing functional deterioration. Information detected by each sensor on the substrate 1 can be transmitted to the laptop computer 32 through two paths, namely, the contact 7 and the BLE module 10. More specifically, a large volume of information detected by the sensors may be transmitted in a shared manner, with less transmission delays.

The multifunctional environmental sensor device 100 includes the substrate 1 and the components including the sensors mounted on the substrate 1, which are accommodated in the front case 14, the rear case 15, the USB cover 16, and the light cover 17. This structure can protect the substrate 1 and the components including the sensors mounted on the substrate 1 from an external impact.

Heat generated by the components including the microphone 4 and the VOC sensor 6 mounted on the substrate 1 and the laptop computer 32 is dissipated outside the front case 14 through the vents 19 in the front case 14. Thus, heat generated by the components is less likely to affect detection performed by the temperature and humidity sensor 2.

The front case 14 includes the L-shaped partition 20. The partition 20 separates the temperature and humidity sensor 2 from the components other than the temperature and humidity sensor 2. This reduces the likelihood of heat generated by the components on the substrate 1 being dissipated by convection toward the temperature and humidity sensor 2. This structure can reduce heat that may affect temperature and humidity detection performed by the temperature and humidity sensor 2.

The substrate 1 receiving the partition 20 has the L-shaped cutout surrounding the temperature and humidity sensor 2. This reduces heat transfer to the temperature and humidity sensor 2 through the substrate 1, reducing such heat affecting temperature and humidity detection performed by the temperature and humidity sensor 2.

The absolute pressure sensor 3, the microphone 4, and the illuminance sensor 5 are mounted between the temperature and humidity sensor 2 and the VOC sensor 6 on the front surface of the substrate 1. Thus, heat generated by the VOC sensor 6 is less likely to affect detection performed by the temperature and humidity sensor 2.

When the protruding end of the multifunctional environmental sensor device 100 is moved forcibly, a portion near the overlap between the extension 21 on the front case 14 and the USB cover 16 comes in contact with the housing of the USB terminal port 31 in the laptop computer 32. The extension 21 and the USB cover 16 overlap each other. The highly rigid overlap between the extension 21 and the USB cover 16 provides strength and reduces, for example, deformation. The portion of the substrate 1 near the USB terminal port 31 is highly likely to be immovable, thus reducing noise in the output from the acceleration sensor 9. The overlap between the extension 21 and the USB cover 16 is located above the contact 7 on the substrate 1. More specifically, the multifunctional environmental sensor device 100 allows effective use of the space above the contact 7, and thus can be downsized while increasing the rigidity of the housing.

The multifunctional environmental sensor device 100 includes the housing with a thickness of about 7 mm and the substrate 1 with a thickness of about 0.8 mm. With the substrate 1 having the thickness of at least 10% of the thickness of the housing, the multifunctional environmental sensor device 100 is rigid. The thickness of the substrate 1 and the heights of the components mounted on the front and back surfaces of the substrate 1 together provide a total thickness of about 32 mm. With the total thickness of the substrate 1 and the components mounted on the front and back surfaces of the substrate 1 being at least 40% of the thickness (about 7 mm) of the housing, the multifunctional environmental sensor device 100 is rigid.

The temperature and humidity sensor 2 is mounted, on the front surface of the substrate 1, at the end opposite to the end with the contact 7. Thus, heat generated by the laptop computer 32 connected through the contact 7 is less likely to affect temperature and humidity detection performed by the temperature and humidity sensor 2.

4. Modifications

The embodiment of the present invention described in detail above is a mere example of the present invention in all aspects. The embodiment may be variously modified or altered without departing from the scope of the present invention. For example, the embodiment may be modified in the following forms. The same components as those in the above embodiment are hereafter given the same numerals, and the operations that are the same as those in the above embodiment will not be described. The modifications described below may be combined as appropriate.

4.1

Figure 10:
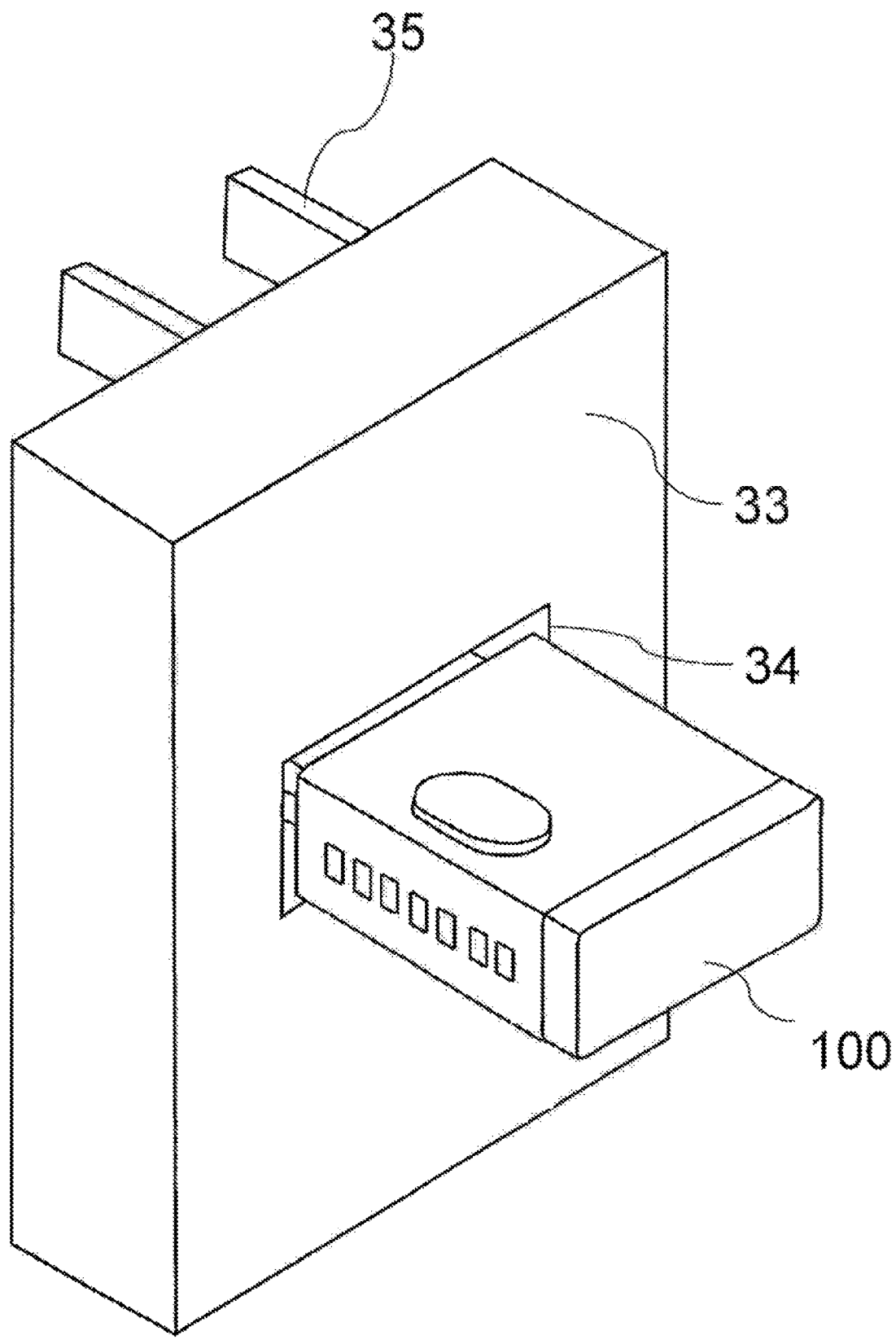
FIG. 10 is a schematic diagram of the multifunctional environmental sensor device connected to a USB connector in an example use.

For example, FIG. 10 is a schematic diagram of the multifunctional environmental sensor device 100 connected to a USB connector 33 in an example use. The USB connector 33 includes a USB terminal 34 and a plug 35 to be plugged into an outlet. The USB connector 33 receiving the multifunctional environmental sensor device 100 is plugged into an outlet with the plug 35 to supply electric power for operating the components on the substrate 1 through the plug 35 and the USB connector 33. Information detected by each sensor mounted on the substrate 1 is transmitted to an external device through the BLE module 10. The multifunctional environmental sensor device 100 described above performs environmental measurements without wiring to the laptop computer 32.

The multifunctional environmental sensor device 100 may include batteries. The multifunctional environmental sensor device 100 described above can operate the sensors without relying on external power supply.

The VOC sensor 6 mounted on the substrate 1 may be replaced by a sensor that can detect a substance in the atmosphere such as carbon monoxide or methane.

The embodiment and the modifications described above may each be combined together.

The elements in the aspects of the present invention below are identified with reference numerals used in the drawings to show the correspondence between these elements and the components in the embodiments.

Aspect 1

A multifunctional environmental sensor device (100) connectable to a terminal (31) of an electronic device (32) for use, the sensor device (100) comprising:
a substrate (1);
a plurality of different types of components mounted on the substrate (1): and
a wiring pattern located on a surface of the substrate (1), the wiring pattern including a contact (7) to be in contact with the terminal of the electronic device.

Aspect 2

The multifunctional environmental sensor device (100) according to aspect wherein
the plurality of components include a light emitter (8) and an illuminance sensor (5), and
the light emitter (8) is mounted on a surface of the substrate (1) opposite to a surface of the substrate (1) on which the illuminance sensor (5) is mounted.

Aspect 3

The multifunctional environmental sensor device (100) according to aspect 2, further comprising:
a cover (17) located over and laterally above the illuminance sensor (5), the cover (17) having a surface with fine irregularities to scatter light.

Aspect 4

The multifunctional environmental sensor device (100) according to any one of aspects 1 to 3, wherein
the plurality of components further include an acceleration sensor (9),
the substrate (1) is substantially rectangular,
the contact (7) is located at a longitudinal end of the substrate (1), and
the acceleration sensor (9) is mounted nearer the contact (7) than a middle of the substrate (1).

Aspect 5

The multifunctional environmental sensor device (100) according to aspect 4, further comprising:
an antenna (13) configured to communicate wirelessly with an external device, wherein the antenna (13) is mounted at an end of the substrate (1) opposite to the end at which the contact (7) is located.

Aspect 6

The multifunctional environmental sensor device (100) according any one of aspects 1 to 5, wherein
on a surface of the substrate (1) opposite to the surface on which the contact (7) is located, a component (11, 12) other than a sensor among the plurality of components is mounted in an area opposite to an area in which the contact (7) is located.

Aspect 7

The multifunctional environmental sensor device (100) according to any one of aspects 1 to 6, wherein
the plurality of components further include a temperature sensor (2),
the multifunctional environmental sensor device (100) further includes a housing (14, 15, 16),
the housing (14, 15, 16) has vents facing each other in surfaces across the substrate (1) in a width direction, and
the temperature sensor (2) is located between the vents.

Aspect 8

The multifunctional environmental sensor device (100) according to aspect 7, wherein
the housing (14, 15, 16) includes a partition (20) separating the temperature sensor (2) from other components.

Aspect 9

The multifunctional environmental sensor device (100) according to aspect 7 or aspect 8, wherein
the plurality of components further include a concentration sensor (6) configured to detect a concentration of a substance in an atmosphere, and a component other than the concentration sensor (6) is at a smallest distance from the temperature sensor (2).

Aspect 10

The multifunctional environmental sensor device (100) according to any one of aspects 7 to 9, wherein
the housing (14, 15, 16) includes
a first housing (16) surrounding the contact (7) to connect to the terminal of the electronic device, and
a second housing (14) accommodating the components other than the contact (7),
the first housing (16) is a hollow polygonal prism,
the second housing (14) includes an engagement part (21) engaged with an inside portion of the first housing (16), and
the first housing (16) and the second housing (14) are fixed to each other with the engagement part (21) being engaged.

The invention claimed is:

1. A multifunctional environmental sensor device connectable to a terminal of an electronic device for use, the sensor device comprising:
a substrate;
a plurality of different types of components mounted on the substrate; and
a wiring pattern located on a surface of the substrate, the wiring pattern comprising a contact to be in contact with the terminal of the electronic device, wherein
the plurality of components comprises an acceleration sensor,
the substrate is substantially rectangular,
the contact is located at a longitudinal end of the substrate, and
the acceleration sensor is mounted nearer the contact than a middle of the substrate, wherein
the plurality of components further comprises a temperature sensor,
the multifunctional environmental sensor device further comprises a housing,
the housing has vents facing each other in surfaces across the substrate in a width direction,
the temperature sensor is located between the vents, and
the housing comprises a partition separating the temperature sensor from other components.

2. The multifunctional environmental sensor device according to claim 1, wherein
the plurality of components comprises a light emitter and an illuminance sensor, and
the light emitter is mounted on a surface of the substrate opposite to a surface of the substrate on which the illuminance sensor is mounted.

3. The multifunctional environmental sensor device according to claim 2, further comprising:
a cover located over and laterally above the illuminance sensor, the cover having a surface with fine irregularities to scatter light.

4. The multifunctional environmental sensor device according to claim 3, further comprising:

an antenna configured to communicate wirelessly with an external device, wherein the antenna is mounted at an end of the substrate opposite to the end at which the contact is located.

5. The multifunctional environmental sensor device according to claim 3, wherein
on a surface of the substrate opposite to the surface on which the contact is located, a component other than a sensor among the plurality of components is mounted in an area opposite to an area in which the contact is located.

6. The multifunctional environmental sensor device according to claim 2, further comprising:
an antenna configured to communicate wirelessly with an external device,
wherein the antenna is mounted at an end of the substrate opposite to the end at which the contact is located.

7. The multifunctional environmental sensor device according to claim 2, wherein
on a surface of the substrate opposite to the surface on which the contact is located, a component other than a sensor among the plurality of components is mounted in an area opposite to an area in which the contact is located.

8. The multifunctional environmental sensor device according to claim 1, further comprising:
an antenna configured to communicate wirelessly with an external device,
wherein the antenna is mounted at an end of the substrate opposite to the end at which the contact is located.

9. The multifunctional environmental sensor device according to claim 1, wherein
on a surface of the substrate opposite to the surface on which the contact is located, a component other than a sensor among the plurality of components is mounted in an area opposite to an area in which the contact is located.

10. The multifunctional environmental sensor device according to claim 1, wherein
the plurality of components further comprises a concentration sensor configured to detect a concentration of a substance in an atmosphere.

11. The multifunctional environmental sensor device according to claim 1, wherein
the housing comprises
a first housing surrounding the contact to connect to the terminal of the electronic device, and
a second housing accommodating the components other than the contact,
the first housing is a hollow polygonal prism,
the second housing comprises an engagement part engaged with an inside portion of the first housing, and
the first housing and the second housing are fixed to each other with the engagement part being engaged.

* * * * *